(12) United States Patent
Sawatari et al.

(10) Patent No.: US 7,794,266 B2
(45) Date of Patent: Sep. 14, 2010

(54) DEVICE AND METHOD FOR REDUCING CROSSTALK

(75) Inventors: Ken Sawatari, San Jose, CA (US); Paul D. Mannheimer, Danville, CA (US); Bradford B Chew, San Ramon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 11/900,853

(22) Filed: Sep. 13, 2007

(65) Prior Publication Data

US 2008/0081492 A1 Apr. 3, 2008

Related U.S. Application Data

(62) Division of application No. 11/540,376, filed on Sep. 29, 2006, now Pat. No. 7,476,131.

(51) Int. Cl.
 *H01R 4/24* (2006.01)
(52) U.S. Cl. ....................................... 439/404
(58) Field of Classification Search ............... 439/83, 439/404, 465, 941, 418; 29/825, 753, 764
 See application file for complete search history.

(56) References Cited

U.S. PATENT DOCUMENTS

| | | | |
|---|---|---|---|
| 3,721,813 A | 3/1973 | Condon et al. | |
| 4,586,513 A | 5/1986 | Hamaguri | |
| 4,603,700 A | 8/1986 | Nichols et al. | |
| 4,621,643 A | 11/1986 | New, Jr. et al. | |
| 4,653,498 A | 3/1987 | New, Jr. et al. | |
| 4,685,464 A | 8/1987 | Goldberger et al. | |
| 4,694,833 A | 9/1987 | Hamaguri | |
| 4,697,593 A | 10/1987 | Evans et al. | |
| 4,700,708 A | 10/1987 | New, Jr. et al. | |
| 4,714,080 A | 12/1987 | Edgar, Jr. et al. | |
| 4,714,341 A | 12/1987 | Hamaguri et al. | |
| 4,752,240 A * | 6/1988 | Jagen et al. | 439/595 |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |

(Continued)

FOREIGN PATENT DOCUMENTS

DE 3516338 11/1986

(Continued)

OTHER PUBLICATIONS

DeKock, Marc; "Pulse Oximetry Probe Adhesive Disks: a Potential for Infant Aspiration," *Anesthesiology*, vol. 89, pp. 1603-1604 (1998).

(Continued)

*Primary Examiner*—Jean F Duverne
(74) *Attorney, Agent, or Firm*—Fletcher Yoder

(57) ABSTRACT

A device and method for reducing crosstalk between wires is provided. The method includes spatially separating first and second sets of wires. A device is disposed relative to the first and second sets of wires to maintain the spatial separation. The method also comprises coupling pins to the first and second sets of wires. Additionally, the method includes covering the device with a connector housing.

18 Claims, 8 Drawing Sheets

U.S. PATENT DOCUMENTS

| | | |
|---|---|---|
| 4,781,195 A | 11/1988 | Martin |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hausman et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,054,488 A * | 10/1991 | Muz ............................ 600/344 |
| 5,055,671 A | 10/1991 | Jones |
| 5,058,588 A | 10/1991 | Kaestle |
| 5,061,207 A * | 10/1991 | Wright ........................ 439/578 |
| 5,065,749 A | 11/1991 | Hasebe et al. |
| 5,066,859 A | 11/1991 | Karkar et al. |
| 5,069,213 A | 12/1991 | Polczynksi |
| 5,078,136 A | 1/1992 | Stone et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H001039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |

| | | | | | |
|---|---|---|---|---|---|
| 5,387,122 A | 2/1995 | Goldberger et al. | 5,630,413 A | 5/1997 | Thomas et al. |
| 5,390,670 A | 2/1995 | Centa et al. | 5,632,272 A | 5/1997 | Diab et al. |
| 5,392,777 A | 2/1995 | Swedlow et al. | 5,632,273 A | 5/1997 | Suzuki |
| 5,398,680 A | 3/1995 | Polson et al. | 5,634,459 A | 6/1997 | Gardosi |
| 5,402,777 A | 4/1995 | Warring et al. | 5,638,593 A | 6/1997 | Gerhardt et al. |
| 5,411,023 A | 5/1995 | Morris, Sr. et al. | 5,638,818 A | 6/1997 | Diab et al. |
| 5,411,024 A | 5/1995 | Thomas et al. | 5,645,060 A | 7/1997 | Yorkey et al. |
| 5,413,099 A | 5/1995 | Schmidt et al. | 5,645,440 A | 7/1997 | Tobler et al. |
| 5,413,100 A | 5/1995 | Barthelemy et al. | 5,660,567 A | 8/1997 | Nierlich et al. |
| 5,413,101 A | 5/1995 | Sugiura | 5,662,105 A | 9/1997 | Tien |
| 5,413,102 A | 5/1995 | Schmidt et al. | 5,662,106 A | 9/1997 | Swedlow et al. |
| 5,417,207 A | 5/1995 | Young et al. | 5,666,952 A | 9/1997 | Fuse et al. |
| 5,421,329 A | 6/1995 | Casciani et al. | 5,671,529 A | 9/1997 | Nelson |
| 5,425,360 A | 6/1995 | Nelson | 5,673,692 A | 10/1997 | Schulze et al. |
| 5,425,362 A | 6/1995 | Siker et al. | 5,673,693 A | 10/1997 | Solenberger |
| 5,427,093 A | 6/1995 | Ogawa et al. | 5,676,139 A | 10/1997 | Goldberger et al. |
| 5,429,128 A | 7/1995 | Cadell et al. | 5,676,141 A | 10/1997 | Hollub |
| 5,429,129 A | 7/1995 | Lovejoy et al. | 5,678,544 A | 10/1997 | DeLonzor et al. |
| 5,431,159 A | 7/1995 | Baker et al. | 5,680,857 A | 10/1997 | Pelikan et al. |
| 5,431,170 A | 7/1995 | Mathews | 5,685,299 A | 11/1997 | Diab et al. |
| 5,437,275 A | 8/1995 | Amundsen et al. | 5,685,301 A | 11/1997 | Klomhaus |
| 5,438,986 A | 8/1995 | Disch et al. | 5,687,719 A | 11/1997 | Sato et al. |
| 5,448,991 A | 9/1995 | Polson et al. | 5,687,722 A | 11/1997 | Tien et al. |
| 5,452,717 A | 9/1995 | Branigan et al. | 5,692,503 A | 12/1997 | Kuenstner |
| 5,465,714 A | 11/1995 | Scheuing | 5,692,505 A | 12/1997 | Fouts |
| 5,469,845 A | 11/1995 | DeLonzor et al. | 5,709,205 A | 1/1998 | Bukta |
| RE35,122 E | 12/1995 | Corenman et al. | 5,713,355 A | 2/1998 | Richardson et al. |
| 5,474,065 A | 12/1995 | Meathrel et al. | 5,724,967 A | 3/1998 | Venkatachalam |
| 5,482,034 A | 1/1996 | Lewis et al. | 5,727,547 A | 3/1998 | Levinson et al. |
| 5,482,036 A | 1/1996 | Diab et al. | 5,731,582 A | 3/1998 | West |
| 5,483,646 A | 1/1996 | Uchikoga | D393,830 S | 4/1998 | Tobler et al. |
| 5,485,847 A | 1/1996 | Baker, Jr. | 5,743,260 A | 4/1998 | Chung et al. |
| 5,490,505 A | 2/1996 | Diab et al. | 5,743,263 A | 4/1998 | Baker, Jr. |
| 5,490,523 A | 2/1996 | Isaacson et al. | 5,746,206 A | 5/1998 | Mannheimer |
| 5,491,299 A | 2/1996 | Naylor et al. | 5,746,697 A | 5/1998 | Swedlow et al. |
| 5,494,032 A | 2/1996 | Robinson et al. | 5,752,914 A | 5/1998 | DeLonzor et al. |
| 5,497,771 A | 3/1996 | Rosenheimer | 5,755,226 A | 5/1998 | Carim et al. |
| 5,499,627 A | 3/1996 | Steuer et al. | 5,758,644 A | 6/1998 | Diab et al. |
| 5,503,148 A | 4/1996 | Pologe et al. | 5,760,910 A | 6/1998 | Lepper, Jr. et al. |
| 5,505,199 A | 4/1996 | Kim | 5,766,125 A | 6/1998 | Aoyagi et al. |
| 5,507,286 A | 4/1996 | Solenberger | 5,766,127 A | 6/1998 | Pologe et al. |
| 5,511,546 A | 4/1996 | Hon | 5,769,785 A | 6/1998 | Diab et al. |
| 5,517,988 A | 5/1996 | Gerhard | 5,772,587 A | 6/1998 | Gratton et al. |
| 5,520,177 A | 5/1996 | Ogawa et al. | 5,774,213 A | 6/1998 | Trebino et al. |
| 5,521,851 A | 5/1996 | Wei et al. | 5,776,058 A | 7/1998 | Levinson et al. |
| 5,522,388 A | 6/1996 | Ishikawa et al. | 5,776,059 A | 7/1998 | Kaestle |
| 5,524,617 A | 6/1996 | Mannheimer | 5,779,630 A | 7/1998 | Fein et al. |
| 5,529,064 A | 6/1996 | Rall et al. | 5,779,631 A | 7/1998 | Chance |
| 5,533,507 A | 7/1996 | Potratz et al. | 5,782,237 A | 7/1998 | Casciani et al. |
| 5,551,423 A | 9/1996 | Sugiura | 5,782,756 A | 7/1998 | Mannheimer |
| 5,551,424 A | 9/1996 | Morrison et al. | 5,782,757 A | 7/1998 | Diab et al. |
| 5,553,614 A | 9/1996 | Chance | 5,782,758 A | 7/1998 | Ausec et al. |
| 5,553,615 A | 9/1996 | Carim et al. | 5,786,592 A | 7/1998 | Hök |
| 5,555,882 A | 9/1996 | Richardson et al. | 5,790,729 A | 8/1998 | Pologe et al. |
| 5,558,096 A | 9/1996 | Palatnik | 5,792,052 A | 8/1998 | Isaacson et al. |
| 5,560,355 A | 10/1996 | Merchant et al. | 5,795,292 A | 8/1998 | Lewis et al. |
| 5,564,417 A | 10/1996 | Chance | 5,797,841 A | 8/1998 | DeLonzor et al. |
| 5,575,284 A | 11/1996 | Athan et al. | 5,800,348 A | 9/1998 | Kaestle |
| 5,575,285 A | 11/1996 | Takanashi et al. | 5,800,349 A | 9/1998 | Isaacson et al. |
| 5,577,500 A | 11/1996 | Potratz | 5,803,910 A | 9/1998 | Potratz |
| 5,582,169 A | 12/1996 | Oda et al. | 5,807,246 A | 9/1998 | Sakaguchi et al. |
| 5,584,296 A | 12/1996 | Cui et al. | 5,807,247 A | 9/1998 | Merchant et al. |
| 5,588,425 A | 12/1996 | Sackner et al. | 5,807,248 A | 9/1998 | Mills |
| 5,588,427 A | 12/1996 | Tien | 5,810,723 A | 9/1998 | Aldrich |
| 5,590,652 A | 1/1997 | Inai | 5,810,724 A | 9/1998 | Gronvall |
| 5,595,176 A | 1/1997 | Yamaura | 5,813,980 A | 9/1998 | Levinson et al. |
| 5,596,986 A | 1/1997 | Goldfarb | 5,817,008 A | 10/1998 | Rafert et al. |
| 5,599,209 A | 2/1997 | Belopolsky | 5,817,009 A | 10/1998 | Rosenheimer et al. |
| 5,601,447 A * | 2/1997 | Reed et al. .................. 439/404 | 5,817,010 A | 10/1998 | Hibl |
| 5,611,337 A | 3/1997 | Bukta | 5,818,985 A | 10/1998 | Merchant et al. |
| 5,617,852 A | 4/1997 | MacGregor | 5,820,550 A | 10/1998 | Polson et al. |
| 5,619,992 A | 4/1997 | Guthrie et al. | 5,823,950 A | 10/1998 | Diab et al. |
| 5,626,140 A | 5/1997 | Feldman et al. | 5,823,952 A | 10/1998 | Levinson et al. |

| | | | | | | |
|---|---|---|---|---|---|---|
| 5,827,182 | A | 10/1998 | Raley et al. | 6,031,603 A | 2/2000 | Fine et al. |
| 5,830,135 | A | 11/1998 | Bosque et al. | 6,035,223 A | 3/2000 | Baker, Jr. |
| 5,830,136 | A | 11/1998 | DeLonzor et al. | 6,036,642 A | 3/2000 | Diab et al. |
| 5,830,137 | A | 11/1998 | Scharf | 6,041,247 A | 3/2000 | Weckstrom et al. |
| 5,839,439 | A | 11/1998 | Nierlich et al. | 6,044,283 A | 3/2000 | Fein et al. |
| RE36,000 | E | 12/1998 | Swedlow et al. | 6,047,201 A | 4/2000 | Jackson, III |
| 5,842,979 | A | 12/1998 | Jarman et al. | 6,061,584 A | 5/2000 | Lovejoy et al. |
| 5,842,981 | A | 12/1998 | Larsen et al. | 6,064,898 A | 5/2000 | Aldrich |
| 5,842,982 | A | 12/1998 | Mannheimer | 6,064,899 A | 5/2000 | Fein et al. |
| 5,846,190 | A | 12/1998 | Woehrle | 6,067,462 A | 5/2000 | Diab et al. |
| 5,851,178 | A | 12/1998 | Aronow | 6,073,038 A | 6/2000 | Wang et al. |
| 5,851,179 | A | 12/1998 | Ritson et al. | 6,078,833 A | 6/2000 | Hueber |
| 5,853,364 | A | 12/1998 | Baker, Jr. et al. | 6,081,735 A | 6/2000 | Diab et al. |
| 5,860,919 | A | 1/1999 | Kiani-Azarbayjany et al. | 6,081,742 A | 6/2000 | Amano et al. |
| 5,865,736 | A | 2/1999 | Baker, Jr. et al. | 6,083,157 A | 7/2000 | Noller |
| 5,871,442 | A | 2/1999 | Madarasz et al. | 6,083,172 A | 7/2000 | Baker, Jr. et al. |
| 5,879,294 | A | 3/1999 | Anderson et al. | 6,088,607 A | 7/2000 | Diab et al. |
| 5,885,213 | A | 3/1999 | Richardson et al. | 6,094,592 A | 7/2000 | Yorkey et al. |
| 5,890,929 | A | 4/1999 | Mills et al. | 6,095,974 A | 8/2000 | Shemwell et al. |
| 5,891,021 | A | 4/1999 | Dillon et al. | 6,104,938 A | 8/2000 | Huiku et al. |
| 5,891,022 | A | 4/1999 | Pologe | 6,112,107 A | 8/2000 | Hannula |
| 5,891,024 | A | 4/1999 | Jarman et al. | 6,113,541 A | 9/2000 | Dias et al. |
| 5,891,025 | A | 4/1999 | Buschmann et al. | 6,115,621 A | 9/2000 | Chin |
| 5,891,026 | A | 4/1999 | Wang et al. | 6,116,965 A | 9/2000 | Arnett et al. |
| 5,902,235 | A | 5/1999 | Lewis et al. | 6,122,535 A | 9/2000 | Kaestle et al. |
| 5,910,108 | A | 6/1999 | Solenberger | 6,133,994 A | 10/2000 | Mathews et al. |
| 5,911,690 | A | 6/1999 | Rall | 6,135,952 A | 10/2000 | Coetzee |
| 5,912,656 | A | 6/1999 | Tham et al. | 6,144,444 A | 11/2000 | Haworth et al. |
| 5,913,819 | A | 6/1999 | Taylor et al. | 6,144,867 A | 11/2000 | Walker et al. |
| 5,916,154 | A | 6/1999 | Hobbs et al. | 6,144,868 A | 11/2000 | Parker |
| 5,916,155 | A | 6/1999 | Levinson et al. | 6,149,481 A | 11/2000 | Wang et al. |
| 5,919,133 | A | 7/1999 | Taylor et al. | 6,150,951 A | 11/2000 | Olejniczak |
| 5,919,134 | A | 7/1999 | Diab | 6,151,107 A | 11/2000 | Schöllermann et al. |
| 5,920,263 | A | 7/1999 | Huttenhoff et al. | 6,151,518 A | 11/2000 | Hayashi |
| 5,921,921 | A | 7/1999 | Potratz et al. | 6,152,754 A | 11/2000 | Gerhardt et al. |
| 5,922,607 | A | 7/1999 | Bernreuter | 6,154,667 A | 11/2000 | Miura et al. |
| 5,924,979 | A | 7/1999 | Swedlow et al. | 6,157,850 A | 12/2000 | Diab et al. |
| 5,924,980 | A | 7/1999 | Coetzee | 6,163,715 A | 12/2000 | Larsen et al. |
| 5,924,982 | A | 7/1999 | Chin | 6,165,005 A | 12/2000 | Mills et al. |
| 5,924,985 | A | 7/1999 | Jones | 6,173,196 B1 | 1/2001 | Delonzor et al. |
| 5,934,277 | A | 8/1999 | Mortz | 6,178,343 B1 | 1/2001 | Bindszus et al. |
| 5,934,925 | A | 8/1999 | Tobler et al. | 6,181,958 B1 | 1/2001 | Steuer et al. |
| 5,940,182 | A | 8/1999 | Lepper, Jr. et al. | 6,181,959 B1 | 1/2001 | Schöllerman et al. |
| 5,954,644 | A | 9/1999 | Dettling et al. | 6,184,521 B1 | 2/2001 | Coffin, IV et al. |
| 5,960,610 | A | 10/1999 | Levinson et al. | 6,186,836 B1 | 2/2001 | Ezawa et al. |
| 5,961,450 | A | 10/1999 | Merchant et al. | 6,188,470 B1 | 2/2001 | Grace |
| 5,961,452 | A | 10/1999 | Chung et al. | 6,192,260 B1 | 2/2001 | Chance |
| 5,964,701 | A | 10/1999 | Asada et al. | 6,195,575 B1 | 2/2001 | Levinson |
| 5,971,930 | A | 10/1999 | Elghazzawi | 6,198,951 B1 | 3/2001 | Kosuda et al. |
| 5,978,691 | A | 11/1999 | Mills | 6,206,830 B1 | 3/2001 | Diab et al. |
| 5,978,693 | A | 11/1999 | Hamilton et al. | 6,213,952 B1 | 4/2001 | Finarov et al. |
| 5,983,122 | A | 11/1999 | Jarman et al. | 6,217,523 B1 | 4/2001 | Amano et al. |
| 5,987,343 | A | 11/1999 | Kinast | 6,222,189 B1 | 4/2001 | Misner et al. |
| 5,991,648 | A | 11/1999 | Levin | 6,226,539 B1 | 5/2001 | Potratz |
| 5,995,855 | A | 11/1999 | Kiani et al. | 6,226,540 B1 | 5/2001 | Bernreuter et al. |
| 5,995,856 | A | 11/1999 | Mannheimer et al. | 6,229,856 B1 | 5/2001 | Diab et al. |
| 5,995,858 | A | 11/1999 | Kinast | 6,230,035 B1 | 5/2001 | Aoyagi et al. |
| 5,995,859 | A | 11/1999 | Takahashi | 6,233,470 B1 | 5/2001 | Tsuchiya |
| 5,997,343 | A | 12/1999 | Mills et al. | 6,236,871 B1 | 5/2001 | Tsuchiya |
| 5,999,834 | A | 12/1999 | Wang et al. | 6,236,872 B1 | 5/2001 | Diab et al. |
| 6,002,952 | A | 12/1999 | Diab et al. | 6,240,305 B1 | 5/2001 | Tsuchiya |
| 6,005,658 | A | 12/1999 | Kaluza et al. | 6,253,097 B1 | 6/2001 | Aronow et al. |
| 6,006,120 | A | 12/1999 | Levin | 6,253,098 B1 | 6/2001 | Walker et al. |
| 6,007,368 | A | 12/1999 | Lorenz et al. | 6,256,523 B1 | 7/2001 | Diab et al. |
| 6,011,985 | A | 1/2000 | Athan et al. | 6,256,524 B1 | 7/2001 | Walker et al. |
| 6,011,986 | A | 1/2000 | Diab et al. | 6,261,236 B1 | 7/2001 | Grimblatov |
| 6,014,576 | A | 1/2000 | Raley et al. | 6,263,221 B1 | 7/2001 | Chance et al. |
| 6,018,673 | A | 1/2000 | Chin et al. | 6,263,222 B1 | 7/2001 | Diab et al. |
| 6,018,674 | A | 1/2000 | Aronow | 6,263,223 B1 | 7/2001 | Sheperd et al. |
| 6,022,321 | A | 2/2000 | Amano et al. | 6,266,546 B1 | 7/2001 | Steuer et al. |
| 6,023,541 | A | 2/2000 | Merchant et al. | 6,266,547 B1 | 7/2001 | Walker et al. |
| 6,026,312 | A | 2/2000 | Shemwell et al. | 6,272,363 B1 | 8/2001 | Casciani et al. |
| 6,026,314 | A | 2/2000 | Amerov et al. | 6,278,522 B1 | 8/2001 | Lepper, Jr. et al. |

| Patent | Date | Inventor |
|---|---|---|
| 6,280,213 B1 | 8/2001 | Tobler et al. |
| 6,280,256 B1 | 8/2001 | Belopolsky et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,321,100 B1 | 11/2001 | Parker |
| 6,325,660 B1 | 12/2001 | Diaz et al. |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,354,872 B1 * | 3/2002 | Lilienthal et al. ........... 439/578 |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| 6,370,408 B1 | 4/2002 | Merchant et al. |
| 6,370,409 B1 | 4/2002 | Chung et al. |
| 6,374,129 B1 | 4/2002 | Chin et al. |
| 6,377,829 B1 | 4/2002 | Al-Ali et al. |
| 6,379,175 B1 | 4/2002 | Reede |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,419,671 B1 | 7/2002 | Lemberg |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |

| | | |
|---|---|---|
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neil et al. |
| 6,752,658 B2 * | 6/2004 | Jones .................. 439/581 |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tscupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckström |
| 6,792,300 B1 | 9/2004 | Diab et al. |
| 6,793,654 B2 | 9/2004 | Lemberg |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,821,142 B1 * | 11/2004 | Rayev et al. ............. 439/418 |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,889,153 B2 | 5/2005 | Dietiker |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,916,289 B2 | 7/2005 | Schnall |
| 6,920,345 B2 | 7/2005 | Al-Ali et al. |
| 6,931,269 B2 | 8/2005 | Terry |
| 6,932,640 B1 * | 8/2005 | Sung .................. 439/405 |
| 6,934,570 B2 | 8/2005 | Kiani et al. |
| 6,939,307 B1 | 9/2005 | Dunlop |
| 6,941,162 B2 | 9/2005 | Fudge et al. |
| 6,947,781 B2 | 9/2005 | Asada et al. |
| 6,950,687 B2 | 9/2005 | Al-Ali |
| 6,963,767 B2 | 11/2005 | Rantala et al. |
| 6,971,580 B2 | 12/2005 | DeLonzor et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,426 B2 | 1/2006 | Yoon et al. |
| 6,992,751 B2 | 1/2006 | Al-Ali |
| 6,992,772 B2 | 1/2006 | Block et al. |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,035,697 B1 | 4/2006 | Brown |
| 7,039,449 B2 | 5/2006 | Al-Ali |
| 7,043,289 B2 | 5/2006 | Fine et al. |
| 7,047,055 B2 | 5/2006 | Boaz et al. |
| 7,047,056 B2 | 5/2006 | Hannula et al. |
| 7,060,035 B2 | 6/2006 | Wasserman et al. |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,117,590 B2 | 10/2006 | Koenig et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,599 B2 | 11/2006 | Terry |
| 7,142,901 B2 | 11/2006 | Kiani et al. |
| 7,162,288 B2 | 1/2007 | Nordstrom |
| 7,190,987 B2 | 3/2007 | Lindekugel et al. |
| 7,198,778 B2 | 4/2007 | Mannheimer et al. |
| 7,209,775 B2 | 4/2007 | Bae et al. |
| 7,210,959 B1 | 5/2007 | Teves |
| 7,215,984 B2 | 5/2007 | Diab et al. |
| 7,225,006 B2 | 5/2007 | Al-Ali et al. |
| 7,236,811 B2 | 6/2007 | Schmitt |
| 7,248,910 B2 | 7/2007 | Li et al. |

| | | | | | | |
|---|---|---|---|---|---|---|
| 7,249,962 B2 * | 7/2007 | Milette et al. ............... 439/425 | | 2004/0143172 A1 | 7/2004 | Fudge et al. |
| 7,254,433 B2 | 8/2007 | Diab et al. | | 2004/0147821 A1 | 7/2004 | Al-Ali et al. |
| 7,254,434 B2 | 8/2007 | Schulz et al. | | 2004/0147822 A1 | 7/2004 | Al-Ali et al. |
| 7,263,395 B2 | 8/2007 | Chan et al. | | 2004/0147823 A1 | 7/2004 | Kiani et al. |
| 7,272,426 B2 | 9/2007 | Scmid | | 2004/0147824 A1 | 7/2004 | Diab et al. |
| 7,280,858 B2 | 10/2007 | Al-Ali et al. | | 2004/0152965 A1 | 8/2004 | Diab et al. |
| 7,295,866 B2 | 11/2007 | Al-Ali et al. | | 2004/0158134 A1 | 8/2004 | Diab et al. |
| 7,305,262 B2 | 12/2007 | Brodnick et al. | | 2004/0158135 A1 | 8/2004 | Baker, Jr. et al. |
| 7,315,753 B2 | 1/2008 | Baker, Jr. et al. | | 2004/0162472 A1 | 8/2004 | Berson et al. |
| 7,371,981 B2 | 5/2008 | Abdul-Hafiz | | 2004/0171920 A1 | 9/2004 | Mannheimer et al. |
| 7,377,794 B2 | 5/2008 | Al-Ali et al. | | 2004/0171948 A1 | 9/2004 | Terry |
| 7,427,165 B2 | 9/2008 | Benaron et al. | | 2004/0176671 A1 | 9/2004 | Fine et al. |
| 2001/0021803 A1 | 9/2001 | Blank et al. | | 2004/0181133 A1 | 9/2004 | Al-Ali et al. |
| 2001/0051767 A1 | 12/2001 | Williams et al. | | 2004/0181134 A1 | 9/2004 | Baker, Jr. et al. |
| 2002/0026109 A1 | 2/2002 | Diab et al. | | 2004/0186358 A1 | 9/2004 | Chernow et al. |
| 2002/0028990 A1 | 3/2002 | Sheperd et al. | | 2004/0199063 A1 | 10/2004 | O'Neil et al. |
| 2002/0038078 A1 | 3/2002 | Ito | | 2004/0204636 A1 | 10/2004 | Diab et al. |
| 2002/0042558 A1 | 4/2002 | Mendelson | | 2004/0204637 A1 | 10/2004 | Diab et al. |
| 2002/0068859 A1 | 6/2002 | Knopp | | 2004/0204638 A1 | 10/2004 | Diab et al. |
| 2002/0128544 A1 | 9/2002 | Diab et al. | | 2004/0204639 A1 | 10/2004 | Casciani et al. |
| 2002/0133067 A1 | 9/2002 | Jackson, III | | 2004/0204865 A1 | 10/2004 | Lee et al. |
| 2002/0156354 A1 | 10/2002 | Larson | | 2004/0210146 A1 | 10/2004 | Diab et al. |
| 2002/0173706 A1 | 11/2002 | Takatani | | 2004/0215069 A1 | 10/2004 | Mannheimer |
| 2002/0173709 A1 | 11/2002 | Fine et al. | | 2004/0230107 A1 | 11/2004 | Asada et al. |
| 2002/0190863 A1 | 12/2002 | Lynn | | 2004/0230108 A1 | 11/2004 | Melker et al. |
| 2002/0198442 A1 | 12/2002 | Rantala et al. | | 2004/0236196 A1 | 11/2004 | Diab et al. |
| 2003/0018243 A1 | 1/2003 | Gerhardt et al. | | 2004/0242980 A1 | 12/2004 | Kiani et al. |
| 2003/0036690 A1 | 2/2003 | Geddes et al. | | 2004/0249252 A1 | 12/2004 | Fine et al. |
| 2003/0045785 A1 | 3/2003 | Diab et al. | | 2004/0257557 A1 | 12/2004 | Block et al. |
| 2003/0073889 A1 | 4/2003 | Keilbach et al. | | 2004/0260161 A1 | 12/2004 | Melker et al. |
| 2003/0073890 A1 | 4/2003 | Hanna | | 2004/0267103 A1 | 12/2004 | Li et al. |
| 2003/0100840 A1 | 5/2003 | Sugiura et al. | | 2004/0267104 A1 | 12/2004 | Hannula et al. |
| 2003/0132495 A1 | 7/2003 | Mills et al. | | 2004/0267140 A1 | 12/2004 | Ito et al. |
| 2003/0135099 A1 | 7/2003 | Al-Ali | | 2005/0004479 A1 | 1/2005 | Townsend et al. |
| 2003/0162414 A1 | 8/2003 | Schulz et al. | | 2005/0010092 A1 | 1/2005 | Weber et al. |
| 2003/0171662 A1 | 9/2003 | O'Connor et al. | | 2005/0020887 A1 | 1/2005 | Goldberg |
| 2003/0176776 A1 | 9/2003 | Huiku | | 2005/0020894 A1 | 1/2005 | Norris et al. |
| 2003/0181799 A1 | 9/2003 | Lindekugel et al. | | 2005/0033128 A1 | 2/2005 | Ali et al. |
| 2003/0187337 A1 | 10/2003 | Tarassenko et al. | | 2005/0033129 A1 | 2/2005 | Edgar, Jr. et al. |
| 2003/0195402 A1 | 10/2003 | Fein et al. | | 2005/0043599 A1 | 2/2005 | O'Mara |
| 2003/0197679 A1 | 10/2003 | Ali et al. | | 2005/0043600 A1 | 2/2005 | Diab et al. |
| 2003/0212316 A1 | 11/2003 | Leiden et al. | | 2005/0049470 A1 | 3/2005 | Terry |
| 2003/0225323 A1 | 12/2003 | Kiani et al. | | 2005/0049471 A1 | 3/2005 | Aceti |
| 2003/0225337 A1 | 12/2003 | Scharf et al. | | 2005/0075550 A1 | 4/2005 | Lindekugel |
| 2003/0236452 A1 | 12/2003 | Melker et al. | | 2005/0079772 A1 | 4/2005 | DeLessert |
| 2003/0236647 A1 | 12/2003 | Yoon et al. | | 2005/0113651 A1 | 5/2005 | Wood et al. |
| 2004/0006261 A1 | 1/2004 | Swedlow et al. | | 2005/0113704 A1 | 5/2005 | Lawson et al. |
| 2004/0010188 A1 | 1/2004 | Wasserman et al. | | 2005/0177034 A1 | 8/2005 | Beaumont |
| 2004/0024297 A1 | 2/2004 | Chen et al. | | 2005/0197548 A1 | 9/2005 | Dietiker |
| 2004/0024326 A1 | 2/2004 | Yeo et al. | | 2005/0228248 A1 | 10/2005 | Dietiker |
| 2004/0034293 A1 | 2/2004 | Kimball | | 2005/0277819 A1 | 12/2005 | Kiani et al. |
| 2004/0039272 A1 | 2/2004 | Abdul-Hafiz et al. | | 2005/0283059 A1 | 12/2005 | Iyer et al. |
| 2004/0039273 A1 | 2/2004 | Terry | | 2006/0058594 A1 | 3/2006 | Ishizuka et al. |
| 2004/0054269 A1 | 3/2004 | Rantala et al. | | 2006/0084852 A1 | 4/2006 | Mason et al. |
| 2004/0054291 A1 | 3/2004 | Schulz et al. | | 2006/0089547 A1 | 4/2006 | Sarussi |
| 2004/0059209 A1 | 3/2004 | Al-Ali et al. | | 2006/0106294 A1 | 5/2006 | Maser et al. |
| 2004/0059210 A1 | 3/2004 | Stetson | | 2006/0195028 A1 | 8/2006 | Hannula et al. |
| 2004/0064020 A1 | 4/2004 | Diab et al. | | 2006/0224058 A1 | 10/2006 | Mannheimer |
| 2004/0068164 A1 | 4/2004 | Diab et al. | | 2006/0241363 A1 | 10/2006 | Al-Ali et al. |
| 2004/0087846 A1 | 5/2004 | Wasserman | | 2006/0247501 A1 | 11/2006 | Ali |
| 2004/0092805 A1 | 5/2004 | Yarita | | 2006/0258921 A1 | 11/2006 | Addison et al. |
| 2004/0097797 A1 | 5/2004 | Porges et al. | | 2006/0276700 A1 | 12/2006 | O'Neil |
| 2004/0098009 A1 | 5/2004 | Boecker et al. | | 2007/0032710 A1 | 2/2007 | Raridan et al. |
| 2004/0107065 A1 | 6/2004 | Al-Ali et al. | | 2007/0032712 A1 | 2/2007 | Raridan et al. |
| 2004/0116788 A1 | 6/2004 | Chernoguz et al. | | 2007/0032715 A1 | 2/2007 | Eghbal et al. |
| 2004/0116789 A1 | 6/2004 | Boaz et al. | | 2007/0073121 A1 | 3/2007 | Hoarau et al. |
| 2004/0117891 A1 | 6/2004 | Hannula et al. | | 2007/0073125 A1 | 3/2007 | Hoarau et al. |
| 2004/0122300 A1 | 6/2004 | Boas et al. | | 2007/0073126 A1 | 3/2007 | Raridan et al. |
| 2004/0122302 A1 | 6/2004 | Mason et al. | | 2007/0073128 A1 | 3/2007 | Hoarau et al. |
| 2004/0133087 A1 | 7/2004 | Ali et al. | | 2007/0123783 A1 | 5/2007 | Chang |
| 2004/0133088 A1 | 7/2004 | Al-Ali et al. | | 2007/0141869 A1 | 6/2007 | McNeely et al. |
| 2004/0138538 A1 | 7/2004 | Stetson | | 2007/0243730 A1 * | 10/2007 | Gladd et al. ............... 439/98 |
| 2004/0138540 A1 | 7/2004 | Baker, Jr. et al. | | 2008/0064940 A1 | 3/2008 | Raridan |

| | | | |
|---|---|---|---|
| 2008/0071153 | A1 | 3/2008 | Al-Ali et al. |
| 2008/0081954 | A1 | 4/2008 | Meyer et al. |
| 2008/0255435 | A1 | 10/2008 | Al-Ali et al. |

FOREIGN PATENT DOCUMENTS

| | | |
|---|---|---|
| DE | 3703458 | 8/1988 |
| EP | 0204259 | 12/1986 |
| EP | 0531631 | 3/1993 |
| JP | 7236625 | 9/1995 |
| JP | 2004159810 | 6/2004 |
| JP | 2004329406 | 11/2004 |
| JP | 2007117641 | 5/2007 |
| WO | WO2005/010568 | 2/2005 |

OTHER PUBLICATIONS

Schulz, Christian Eric; "Design of a Pulse Oximetry Sensor Housing Assembly," California State University Master's Thesis, *UMI Dissertation Services*, UMI No. 1401306, (May 2000) 63 pages.

Yokota, Nakaura, Takahashi, et al.; "Pilot Model of Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.

Irie., A., et al.; "Respiration Monitors—Pulse Oximeters," *Neonatal Care*, vol. 15, No. 12, pp. 78-83 (2002) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Urquhart, C., et al.; "Ear probe pulse oximeters and neonates," *Anaesthesia*, vol. 60, p. 294 (2005).

* cited by examiner

DEVICE AND METHOD FOR REDUCING CROSSTALK

PRIORITY CLAIM

This application is a divisional of U.S. application Ser. No. 11/540,376, filed on Sep. 29, 2006, and issued as U.S. Pat. No. 7,476,131 on Jan. 13, 2009.

TECHNICAL FIELD

The present invention relates generally to electronic devices, such as medical devices, and more particularly to reducing crosstalk in such devices.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Medical devices such as those used for monitoring a patient's vital sign or other physiologic variable, are commonly comprised of a patient-contacting signal transducer and a monitor that connects to the transducer, processes the signals, and provides information to the caregiver. Typically, the transducer is connected to the monitor with and interface cable that includes wires for conducting electrical signals.

An ideal cable and connector assembly for use in such medical devices would be immune to noise interference from external sources as well as crosstalk between wires within the cable and connector assembly. In reality, however, the manufacturing process of a cable and connector assembly includes steps that make the wires within a cable and connector assembly vulnerable to noise, such as capacitive and inductive crosstalk, wherein electrical signals in one wire or pair of wires may interfere or create noise on a nearby wire. The crosstalk may be detrimental to the operation of a medical device. For example, in pulse oximetry, the crosstalk can result in inaccurate readings of $SpO_2$ values.

Cables are generally manufactured to limit the amount of external noise and inductive and capacitive crosstalk that can occur between wires. For example, the cables are bundled together with an electrically insulating protective coating and a conductive shield mesh to protect against environmental noise sources. Additionally, the cables may be made up of twisted wire pairs, commonly referred to as twisted pairs. As their name suggests, the twisted pairs are a pair of wires twisted together in a manner that results in each wire becoming exposed to the same or similar amounts noise elements such that the noise can be nearly or completely canceled out. A twisted pair may be surrounded by an electrically grounded conductive mesh shield to help eliminate noise interference from other wires within the cable bundle. Twisted pairs having the conductive mesh shield are referred to as shielded twisted pairs, while twisted pairs without the conductive mesh are referred to as unshielded twisted pairs. The cables used in medical devices such as pulse oximetry systems are commonly constructed with one or both types of twisted pairs, where multiple sets of wires are combined into a cable bundle. Electrical crosstalk can occur when signal wires electrically contact one another (a "short"), or come into close proximity to adjacent conductors.

In order to connect the wires to connector pins, the cable bundle must be stripped and the wires untwisted. Thus, in this section of the cables, the wires are unprotected and vulnerable to crosstalk interference. Furthermore, after the wires have been connected to connector pins and the pins are placed in a connector housing, even if the wires are initially pushed apart and spatially separated, additional handling and processing may push the wires together and increase the likelihood of crosstalk.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a medical device cable. In the examples used herein, the medical device is a pulse oximeter. The pulse oximeter cable comprises a first pair of wires, a second pair of wires and an insulative piece configured to maintain spatial separation between the first and second pairs of wires. Additionally, the cable comprises a connector housing formed over the insulative piece.

In accordance with another aspect of the present invention, there is provided a method of manufacturing an electrical cable comprising spatially separating a first set of wires from a second set of wires and disposing a device relative to the first and second sets of wires to maintain the spatial separation and coupling pins to the first and second sets of wires. Additionally, the method comprises covering the device with a connector housing.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
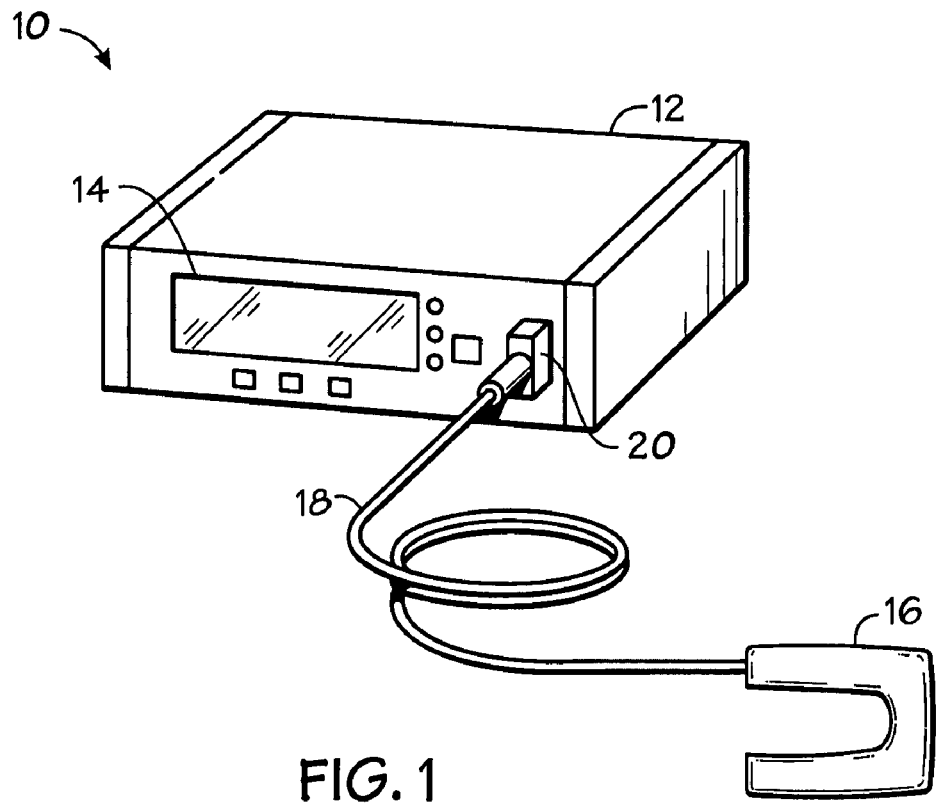
FIG. 1 illustrates an exemplary pulse oximetry system in accordance with an exemplary embodiment of the present invention.

Turning initially to FIG. 1, an exemplary medical device, such as a pulse oximetry system, is illustrated and generally designated by the reference numeral 10. Pulse oximetry systems, such as system 10, calculate various physiological parameters by detecting electromagnetic radiation (light) that is scattered and absorbed by blood perfused tissue. The pulse oximeter system 10 has a main unit 12 which houses hardware and software configured to calculate various physiological parameters. The main unit 12 has a display 14 for displaying the calculated physiological parameters, such as oxygen saturation or pulse rate, to a caregiver or patient. The pulse oximetry system 10 also has a sensor unit 16, which may take various forms. As shown in FIG. 1, the sensor unit 16 may be configured to fit over a digit of a patient or a user. The sensor unit 16 is connected to the main unit 12 via a cable 18. The cable 18 may be coupled to main unit 12 using a connector housing 20. It is at the interface between the cable 18 and the pins 34 (shown in FIG. 2) of the connector housing 20 where noise interference in the form of crosstalk is most likely to occur.

Figure 2:
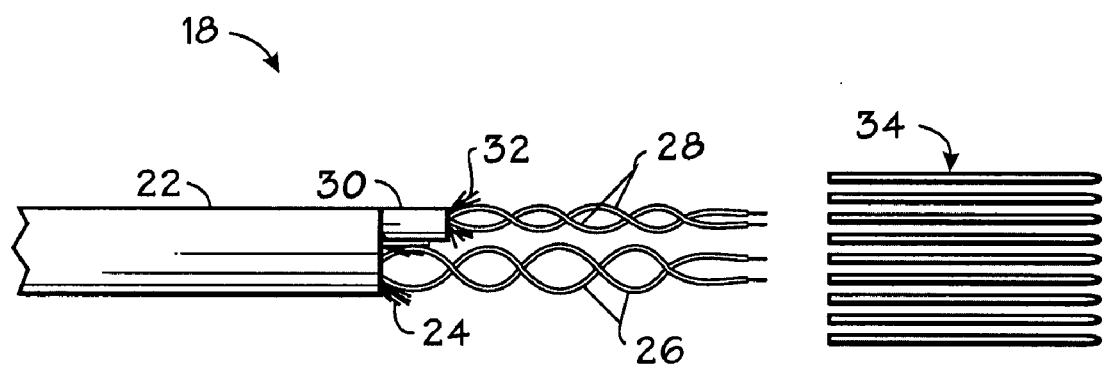
FIG. 2 illustrates a pulse oximetry cable in accordance with an embodiment of the present invention.

A more detailed illustration of the cable 18 is shown in FIG. 2. Specifically, the cable 18 is shown having an outer jacket 22. The outer jacket 22 is a polymeric material jacket to hold the cable bundle together and to protect the wires from environmental factors. Under the outer jacket 22, the cable 18 has an outer shield 24 which may be configured to prevent electromagnetic interference from external sources. The outer shield 24 may be made up any type of shielding material, such as a metallic mesh, for example.

The cable 18, as shown in FIG. 2, has both emitter wires 26 and detector wires 28. Both the emitter wires 26 and the detector wires 28 are twisted pair wires. The wire pairs are twisted so that each wire is similarly exposed to any potential electromagnetic interference that reaches the wires. Because each of the wires is exposed to similar levels of interference, the interference can be reduced through circuit designs that cancel such common-mode signals.

The emitter wires 26 may comprise an unshielded twisted pair and the detector wires 28 may comprise a shielded twisted pair. As can be seen in FIG. 2, the detector wires 28 have a jacket 30, such as a polymeric coating for example, and an inner shield 32 similar to the outer shield 24 of the cable 18. The detector wires 28 are shielded electrically to prevent potential crosstalk from the emitter wires 26, as well as interference from environmental factors. Both the emitter wires 26 and the detector wires 28 are individually connected to respective pins 34 of a connector housing, such as connector housing 20.

During the manufacturing process, the outer jacket 22 is stripped from the cable 18, and the coating 30 of the detector wires 28 is stripped from the detector wires 28. The emitter wires 26 and detector wires 28 are then untwisted to facilitate connection of the emitter wires 26 and detector wires 28 to their respective pins 34. The detector wires 28, however, become vulnerable to a variety of noise-inducing influences, including inductive and capacitive crosstalk from the emitter wires 26 when they are unshielded and untwisted.

Initially, during the manufacturing process, the emitter wires 26 and the detector wires 28 are separated. The wires may be pulled apart by a worker or a machine may push a tool in between the pairs of wires to separate them. Unfortunately, after this initial separation, little may be done to maintain the separation of the wires.

Although workers may understand their specific role in the manufacturing process, they may not fully appreciate the importance of maintaining the separation between the wires and may fail to take precautions to maintain the separation of the wires. As such, the cables may be tossed into bins for transportation to different workstations, and the cables may be handled and manipulated by multiple workers and machines before the cables are fully assembled and ready for operation. In the bins, the cables may be compacted together or get tangled together. While being handled and manipulated by workers and machines, the wires may be pushed together. Therefore, at the end of the manufacturing process, there is a risk that the wires will no longer be separated, resulting in an increased susceptibility to crosstalk in the fully assembled cables.

Figure 3:
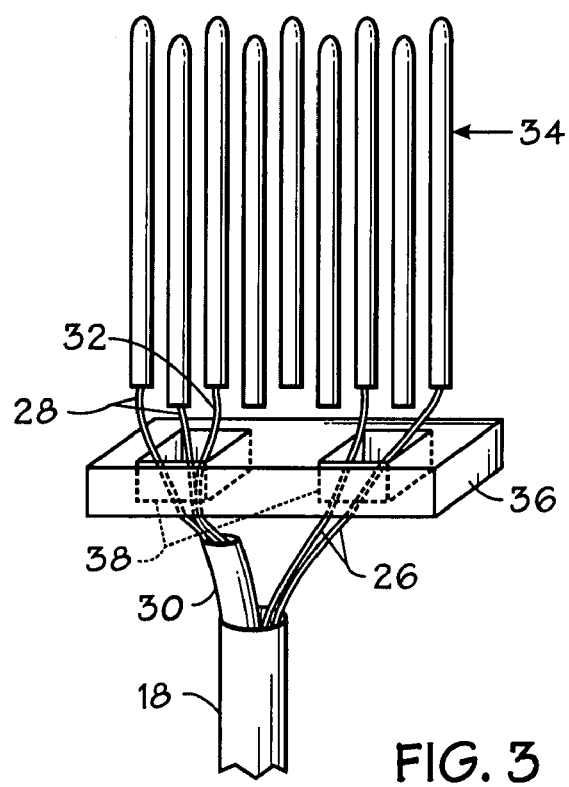
FIG. 3 illustrates an insulative material with slots through which wires pass in accordance with an exemplary embodiment of the present invention.

To address this concern, an insulative material 36, as illustrated in FIG. 3, may be used to maintain spatial separation between the emitter wires 26 and detector wires 28 in order to prevent crosstalk. The insulative material 36 may be a silicon rubber, polymer, or other electrically non-conductive material. The insulative material 36 may have apertures 38, such as slots, through which the emitter wires 26 and detector wires 28 are passed during the manufacturing process. The wires may be coupled to the pins before or after being passed through the apertures 38. The apertures 38 of the insulative material 36 help ensure that the emitter wires 26 and detector wires 28 remain separated throughout the manufacturing process to prevent crosstalk.

After the emitter wires 26 and detector wires 28 have been positioned in the apertures 38, the insulative material 36 and a portion of the pins 34 and the wires 26 and 28 are encapsulated by the connector housing 20. An over-molding process (such as insert, injection, or transfer molding), or other means, may be implemented to form the connector housing 20. The connector housing 20 is formed over the insulative piece 36 so that the insulative piece 36 can continue to prevent the emitter and detector wires from moving closer to each other during the encapsulation process. By preserving the spatial separation, the insulative piece 36 helps the detector wires 28 to be less susceptible to crosstalk interference from the emitter wires 26.

Figure 4:
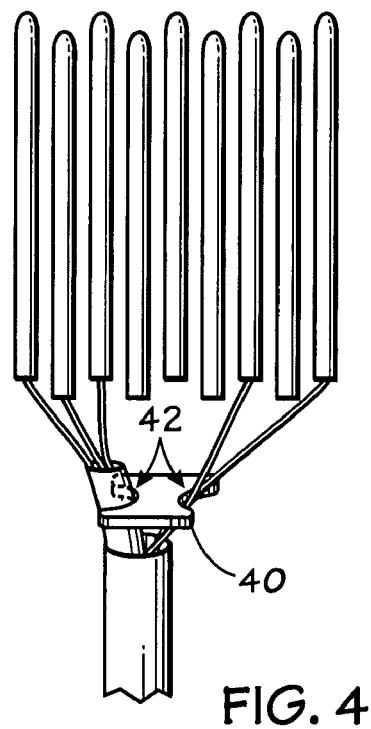
FIG. 4 illustrates an insulative piece between wires in accordance with an alternative exemplary embodiment of the present invention.

In another embodiment, as illustrated in FIG. 4, an insulative piece 40, such as a piece of silicon rubber, polymer or other electrically non-conductive material, may be wedged or coupled between the emitter wires 26 and detector wires 28 to prevent electrical crosstalk. The insulative piece 40 is wedged or coupled between the emitter wires 26 and detector wires 28 by directing the wires into open ended apertures 42 located on opposite sides of the insulative piece 40. The insulative piece 40 is installed prior to the encapsulation process and prevents the emitter wires 26 and the detector wires 28 from moving into closer proximity of each other during the encapsulation process or handling prior during the manufacturing process. The encapsulation process forms the connector housing 20 over the insulative piece 40, as described above.

Figure 5:
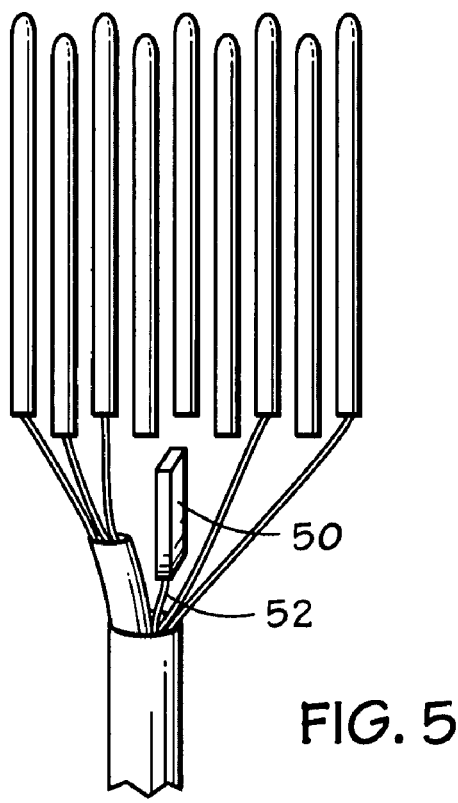
FIG. 5 illustrates an electrically grounded conductive object between wires in accordance with an alternative exemplary embodiment of the present invention.

Alternatively, as illustrated in FIG. 5, a conductive object 50, such as a piece of copper, positioned between the emitter wires 26 and detector wires 28 can help reduce or eliminate crosstalk. The conductive object 50 is electrically grounded via the wire 52. The wire 52 may be formed by aggregating the wire mesh of the outer shield 24 to form a single wire, or comprise a separate drain or ground wire. The conductive object 50 is positioned between the emitter wires 26 and detector wires 28. It should be understood that the conductive object 50 may be implemented alone or in conjunction with insulative embodiments described herein. Specifically, for example, the conductive object 50 may be supported by the insulative material 36 of FIG. 3. The connector housing 20 would then be formed over the both conductive object 50 and the insulative material 36.

Figure 6:
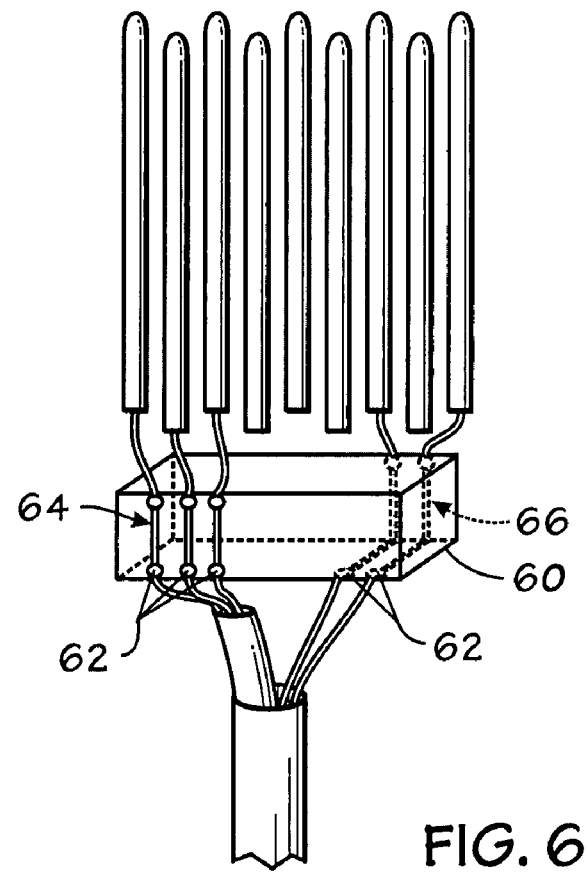
FIG. 6 illustrates an insulative block with pads and traces configured to spatially separate wires in accordance with an alternative exemplary embodiment of the present invention.

Turning to FIG. 6, yet another embodiment includes an insulative piece 60 with solder pads 62 and traces 64 and 66. The insulative piece 60 may be a resin glass composition, a polymer capable of withstanding the temperatures used in soldering, or other suitable material. As illustrated, the insulative piece 60 has solder pads 62 on one side to connect the emitter wires 26 and detector wires 28 to the insulative piece 60. The solder pads 62 are connected to electrically conductive traces 64 and 66 that run on the front side and backside of the insulative piece 60, respectively. Specifically, the traces 64, which are coupled to the detector wires 28, run on a front side of the insulative piece 60, while the traces 66, which are coupled to the emitter wires 26, run on a backside of the piece 60. Thus, the insulative piece 60 spatially separates the emitter traces 26 from the detector traces 28 to prevent crosstalk from occurring. Once the wires and pins are coupled to the insulative piece, the connector housing 20 may be formed over the insulative piece 60 through the encapsulation process.

Figure 7:
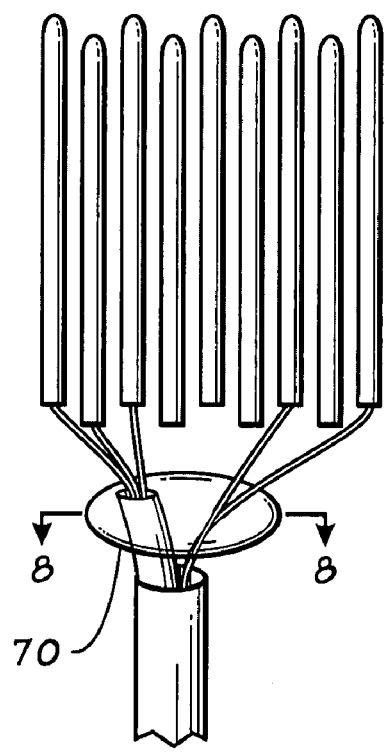
FIG. 7 illustrates placing an epoxy material on and in between wires in accordance with an alternative exemplary embodiment of the present invention.

Alternatively, an insulative material 70, such as epoxy resin or silicone, for example, may be used to maintain spatial separation of the detector wires 28 and the emitter wires 26, as illustrated in FIG. 7. The material 70 may be placed on and in between the wires 26 and 28 after the external coating has been removed and the wires 26 and 28 have been separated from each other. The material 70 may initially be a two-part gel that cures and hardens as the two parts interact. Once cured, the material 70 holds the wires in place to prevent the wires from coming into proximity of each other during the manufacturing process.

Figure 8:
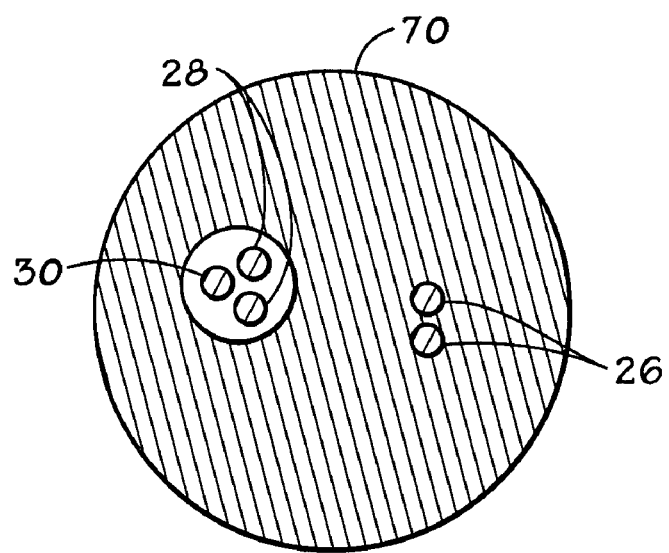
FIG. 8 illustrates a cross-sectional view of the material of FIG. 7.

A cross-sectional view of the material 70 is illustrated in FIG. 8. As can be seen, the detector wires 28 are spatially separated from the emitter wires 26. The material 70 has a high dielectric constant to reduce capacitive effects, and, therefore, the emitter wires 26 and the detector wires are spatially and electrically isolated. The connector housing 20 may be formed over the material 70 through the encapsulation process after the material 70 has cured.

Figure 9:
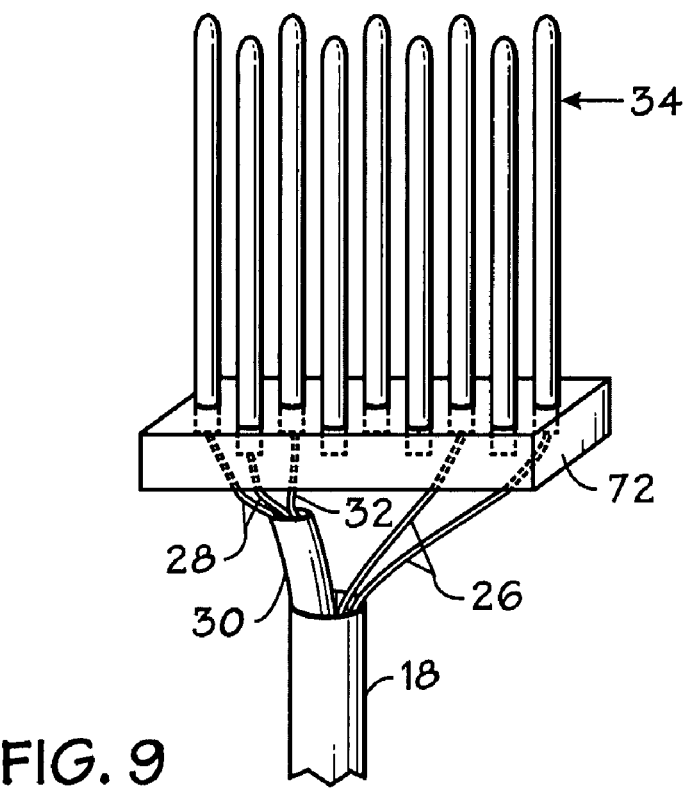
FIG. 9 illustrates a printed circuit board configured to spatially separate wires in accordance with an alternative exemplary embodiment of the present invention.

In another embodiment, a printed circuit board (PCB) 72 may also be used to maintain spatial separation between the emitter wires 26 and detector wires 28, as shown in FIG. 9. The PCB 72 may be a multi-layer PCB with solder pads or holes (not shown) for coupling the wires to the PCB 72. The solder pads or holes for coupling the emitter wires 26 to the PCB 72 may be located remotely from the solder pads or holes for coupling the detector wires 28 to the PCB 72. Vias and traces in and on the PCB 72 connect the emitter wires 26 and detector wires 28 to the proper pins. The connector housing 20 may be formed over the PCB 72.

Figure 10:
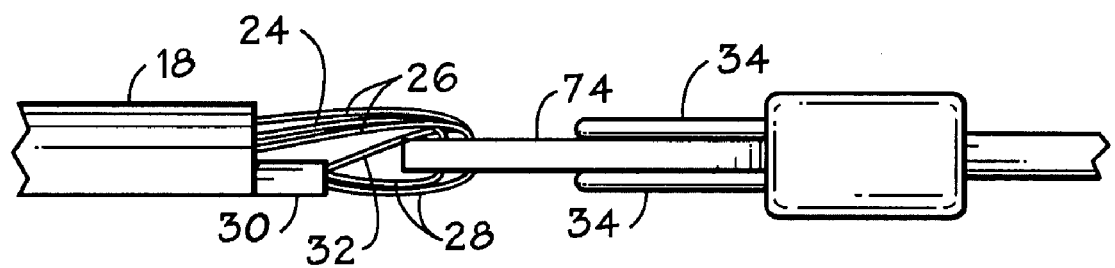
FIG. 10 illustrates an alternative embodiment for using a printed circuit board in accordance with an alternative exemplary embodiment of the present invention.
Figure 11:
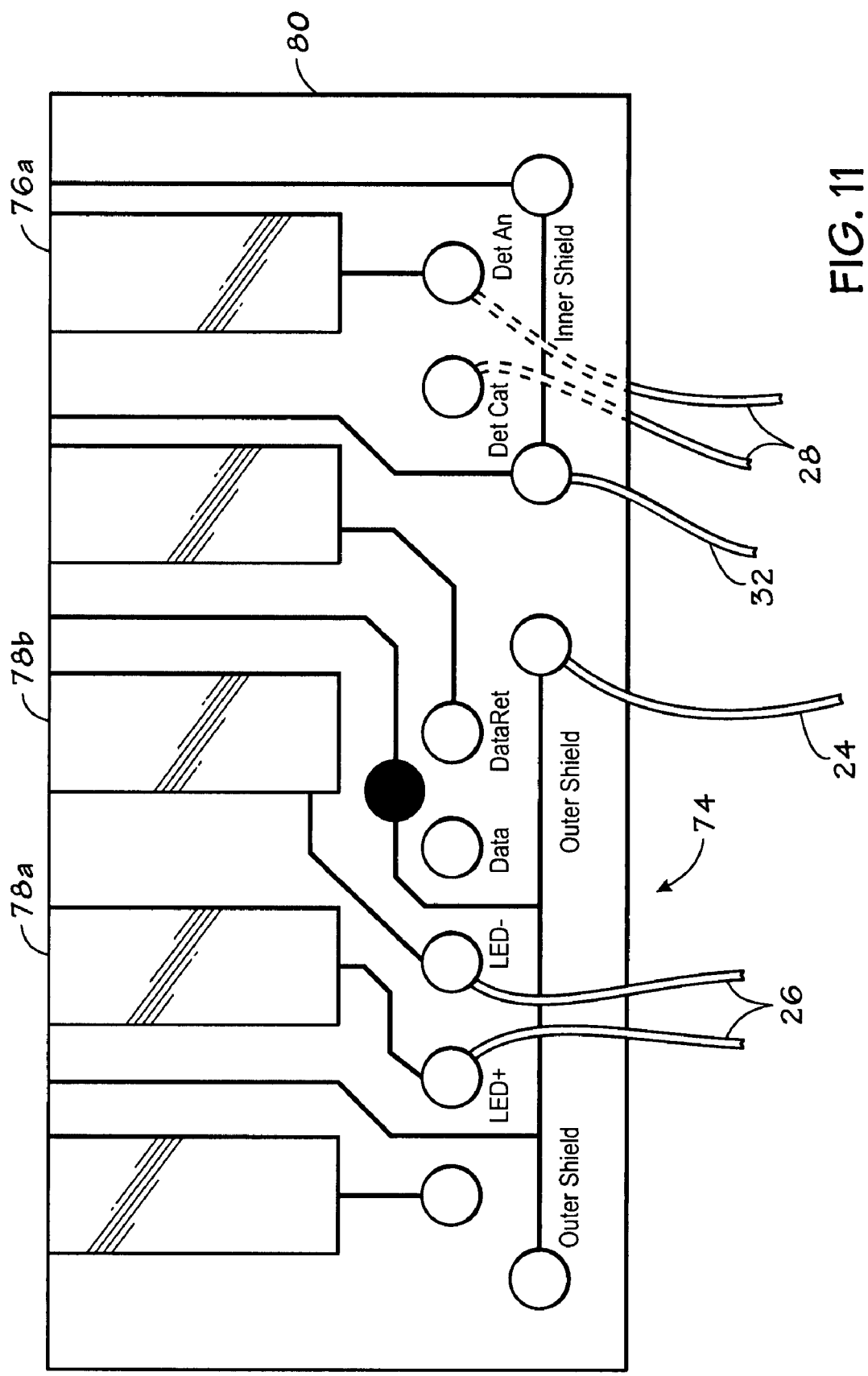
FIG. 11 illustrates top view of the printed circuit board of FIG. 10.
Figure 12:
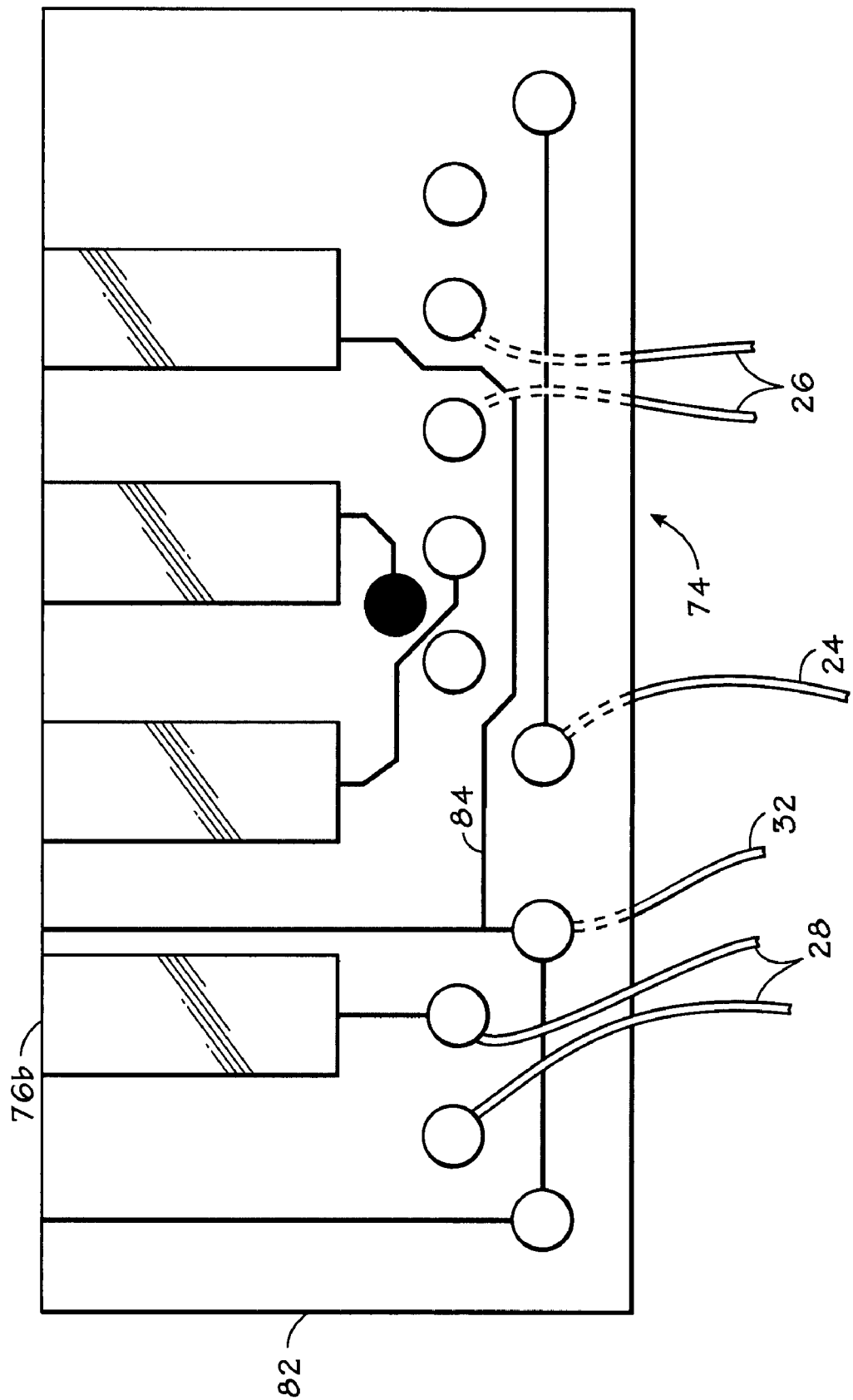
FIG. 12 illustrates a view of the bottom of the printed circuit board of FIG. 10.

An alternative embodiment using a PCB to prevent crosstalk is shown in FIG. 10. Specifically, FIG. 10 shows a side view of a PCB 74 positioned between a top layer and a bottom layer of pins 34. The PCB 74 is a two layer circuit board having traces, pads, and connection points for the connector pins 34 on both layers of the PCB 74. As can be seen by further referring to FIGS. 11 and 12, the detector contacts 76a-b are physically remote from the emitter contacts 78a-b. In addition, the inner shield wire 32 is soldered on the top layer 80 of the PCB 74 while the detector wires 28 are soldered on the bottom layer 82 of the PCB 74. The location of the detector wires 28 provide spatial separation from the emitter wires 26. The PCB 74 additionally shields the detector contacts 76a-b and emitter contacts 78a-b from the memory chip contacts. The inner shield 32 is routed to pin 6 by a trace 84. The connector housing 20 may be formed over the PCB 74. Wires 26 and 28 emanating from cable 18 may be kept short in length to prevent cross-talk. Use of the PCB provides an easier substrate to terminate the wires to during the manufacturing process than terminating the wires to the pins directly.

Figure 13:
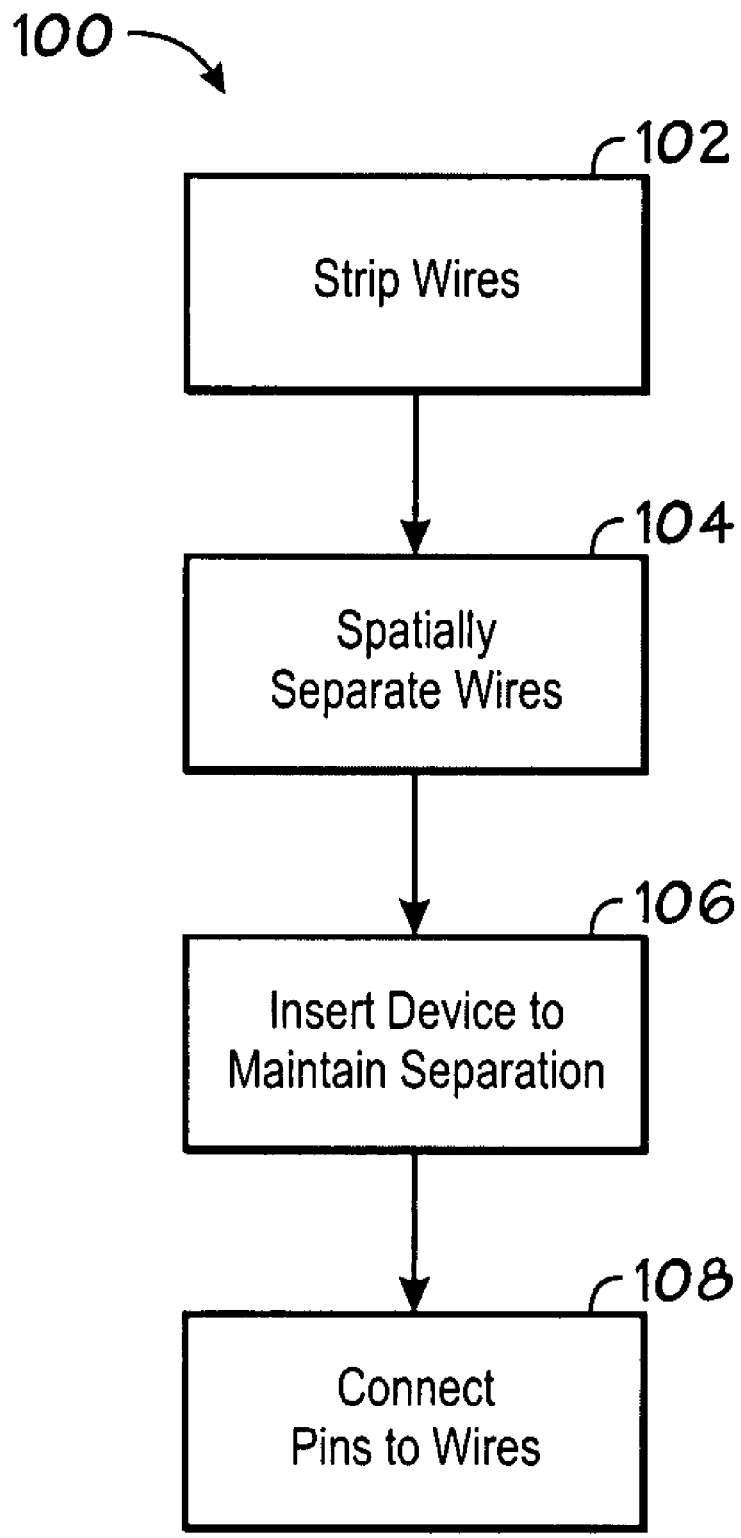
FIG. 13 is a flow chart depicting a technique for reducing crosstalk in accordance with an exemplary embodiment of the present invention.

Turning to FIG. 13, a technique to prevent crosstalk in pulse oximetry cables in accordance with an exemplary embodiment of the present invention is illustrated as a flow chart and generally designated by the reference numeral 100. The technique 100 begins by stripping a cable, as indicated at block 102. The cable may be any cable used in medical devices, such as those used in pulse oximeters and may include multiple wires which are also stripped. Once stripped, the wires are vulnerable to potential noise-inducing influences, such as crosstalk from the other wires of the cable. Therefore, the stripping of the wires should be performed with the goal of preserving as much of the shield on the wires as possible.

After the wires are stripped, the wires are spatially separated from each other, as indicated at block 104. Specifically, sets of twisted pairs are separated from each other. The spatial separation of the wires may be done by a person or by a machine. Because the twisting of the wires is a noise cancellation technique, effort should be made to keep the pairs of wires twisted, insofar as it is practicable.

The spatial separation between the sets of wires is maintained by coupling or inserting a device between the sets of wires, as indicated at block 106. Specifically, the spatial separation may be maintained by implementing one of the embodiments described above, such as using a PCB to physically separate the emitter wires 26 from the detector wires 28, for example, or inserting an insulative object between the pairs of wires. The use of one of the above mentioned exemplary embodiments, or other device, precludes the pushing of the separated wires into closer proximity of each other during the over-molding process or other processing and handling that may occur during manufacture.

Connector pins are electrically coupled to the wires, as indicated by block 108. The connector pins may be connected to the wires either directly by soldering the wires to the pins or indirectly via traces on a PCB, as described above, depending on the particular embodiment being implemented. By physically separating the wires and preserving that separation, crosstalk between wires is greatly reduced, or eliminated. The elimination of crosstalk may increase the accuracy of the medical devices.

The techniques described herein for maintaining spatial separation of the signal wires during the cable termination process to reduce cross-talk have applicability in patient monitoring applications beyond pulse oximetry. With respect to devices that utilize photo-emitters and photo-detectors as described herein, such techniques can be utilized in devices intended to monitor other blood constituents such as carboxy-hemoglobin, methemoglobin, total hemoglobin content, glucose, pH, water content and others. Reducing signal cross-talk is also of importance in bio-impedance measurements for evaluating physiologic variables such as tissue hydration, cardiac output or blood pressure.

The step of creating a cabling connector may not be restricted to over-molding processes. Pre-molded connector housing components may be assembled to contain the pins and cable. During assembly, wires may come into close proximity that results in cross-talk (noise). The techniques described above may be used to reduce the likelihood of this occurring by ensuring proper spatial separation during the assembly process.

Additionally, it should be understood, that although the figures and the associated discussion describe embodiments wherein the cable 18 comprises twisted pair wires, the techniques disclosed herein may be applicable to any type of cable. Indeed, the techniques disclosed herein may be implemented with a coaxial cable, for example.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of manufacturing an electrical cable comprising:
   spatially separating a first set of wires from a second set of wires;
   disposing an insulative member relative to the first and second sets of wires to maintain complete spatial separation of the first and second set of wires as the first and second set of wires pass through the insulative member;
   coupling pins to the first and second sets of wires; and
   completely surrounding the insulative member with a separate connector housing.

2. The method of claim 1, wherein disposing the insulative member comprises passing the first set of wires through a first aperture of the insulative member and passing the second set of wires through a second aperture of the insulative member.

3. The method of claim 1, wherein disposing the insulative member comprises disposing the first set of wires in an first open ended aperture on a first side of the insulative member and disposing the second set of wires in a second open ended aperture on a second side of the insulative member.

4. The method of claim 1, wherein disposing the insulative member comprises disposing a conductive piece in between the wires, the conductive piece being coupled to ground.

5. The method of claim 1, wherein disposing the insulative member comprises disposing the wires in a dielectric gel and allowing the gel to cure while the wires are spatially separated.

6. The method of claim 1, comprising stripping the cable to expose the first and second sets of wires.

7. The method of claim 1, wherein completely surrounding the insulative member with a separate connector housing comprises an over-molding process.

8. The method of claim 1, wherein completely surrounding the insulative member with a separate connector housing comprises an assembly of pre-configured components.

9. The method of claim 1, comprising stripping internal electrical isolation insulation from the first set of wires.

10. A method of manufacturing an electrical cable comprising:
    spatially separating a first set of wires from a second set of wires;
    disposing a device relative to the first and second sets of wires to maintain the spatial separation, wherein disposing the device comprises coupling the first and second sets of wires to the device, wherein the device comprises a printed circuit board;
    coupling pins to the first and second sets of wires; and
    completely surrounding the device with a separate connector housing.

11. The method of claim 10, comprising coupling the pins to the printed circuit board to electrically couple the first and second sets of wires to the pins.

12. The method of claim 11, wherein coupling the pins to the printed circuit board comprises inserting the printed circuit board in between the pins and soldering the pins to the printed circuit board.

13. A method of manufacturing an electrical cable comprising:
    spatially separating a first set of wires from a second set of wires;
    disposing a device relative to the first and second sets of wires to maintain the spatial separation, wherein disposing the device comprises coupling the first and second sets of wires to an insulative object, the insulative object having a first set of conductive traces disposed on a first side of the insulative object and a second set of conductive traces disposed on a second side of the insulative object;
    coupling pins to the first and second sets of wires; and
    completely surrounding the device with a separate connector housing.

14. A method of manufacturing a cable connector comprising:
    stripping internal electrical isolation insulation from a first set of wires of a cable;
    inserting the first set of wires through a first hole of an insulative member; and
    inserting a second set of wires of the cable through a second hole of an insulative member to completely spatially separate the first set of wires from the second set of wires as the first and second set of wires pass through the insulative member;
    coupling pins to the first and second sets of wires; and
    completely covering the insulative member with a separate connector housing.

15. The method of claim 14, wherein completely covering the insulative member with a separate connector housing comprises an over-molding process.

16. The method of claim 14, wherein stripping the internal electrical isolation insulation from a first set of wires comprises removing a metallic mesh surrounding the first pair of wires.

17. The method of claim 14, comprising stripping insulation surrounding both the first and second sets of wires.

18. The method of claim 17, wherein stripping insulation surrounding both the first and second sets of wires comprises removing a metallic mesh that surrounds both the first and second sets of wires.

* * * * *